United States Patent
Torgerson et al.

(10) Patent No.: US 6,361,551 B1
(45) Date of Patent: Mar. 26, 2002

(54) COLLAGEN HEMOSTATIC FIBERS

(75) Inventors: Robert D. Torgerson, Wakefield; John Uhoch, Warwick, both of RI (US); Francis B. Maddalo, Needham, MA (US); Stephen N. Eldridge, Cranston, RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/209,723

(22) Filed: Dec. 11, 1998

(51) Int. Cl.$^7$ .............................. A61B 17/08; A61D 1/00

(52) U.S. Cl. ...................................................... 606/214

(58) Field of Search ............................. 606/214, 229, 606/228, 215; 604/368, 230, 367, 369; 424/423, 424, 425, 426; 106/160.1; 530/356

(56) References Cited

U.S. PATENT DOCUMENTS

| | | |
|---|---|---|
| 505,148 A | 9/1893 | Weaver |
| 2,598,608 A | 5/1952 | Salo et al. |

(List continued on next page.)

FOREIGN PATENT DOCUMENTS

| | | |
|---|---|---|
| DE | 1469075 | 12/1968 |
| EP | 083 868 | 12/1982 |
| EP | 0 310 623 | 12/1987 |
| EP | 0 463 887 | 1/1992 |
| EP | 0 552 576 | 2/1998 |
| GB | 831124 | 3/1960 |
| WO | WO 93/06791 | 4/1993 |
| WO | WO 95/25482 | 9/1995 |
| WO | WO 95/25550 | 9/1995 |

OTHER PUBLICATIONS

Braun Product Insert on Web Page for Osteovit® collagen matrix for filling bone defects (one page).
Braun Product Insert on Web Page for Lyostypt® local haemostatic agent (one page).
Bloom W et al. *A Textbook of Histology*; Ninth Ed.; WB Saunders, Philadephia, 1970; see pp. 223–224.
Chvapil M., "Collagen Sponge Theory and Practice of Medical Applications," J. Biomed Mater. Res., vol. 11:721–741 (1977).
Silverstein ME et al., "Collagen Fibers as a Fleece Hemostatic Agent," J. Trauma, vol. 20: 688–694 (1980).
Silverstein ME et al., "Experimental and Clinical Experiences with Collagen Fleece as a Hemostatic Agent," J. Trauma, vol. 21, No. 5: 388–393 (1981).
Coln D, et al., "Evaluation of Hemostatic Agents in Experimental Splenic Lacerations," Am J. Surg., vol. 145: 256–259 (1983).
Kato et al., "Formation of Continuous Collagen Fibres: Evaluation of Biocompatibility and Mechanical Properties," Biomaterials, (1990) vol. 11, No. 3, pp. 169–175.

(List continued on next page.)

Primary Examiner—Henry J. Recla
Assistant Examiner—Vy Q. Bui
(74) Attorney, Agent, or Firm—Wolf, Greenfield & Sacks, P.C.

(57) ABSTRACT

A collagen fiber and methods for producing and using the collagen fiber of the inventions to prepare hemostatic fabrics to control bleeding are provided. The collagen particles (e.g., fibrils) of the fiber, preferably, have a hemostatic activity that is equivalent to the hemostatic activity of the collagen particles from which the fiber is formed. The collagen fibers of the invention and hemostatic fabrics formed thereof optionally include hemostatic agents and/or other therapeutic agents, to further promote hemostasis and wound healing.

83 Claims, 1 Drawing Sheet

U.S. PATENT DOCUMENTS

| | | | |
|---|---|---|---|
| 2,637,321 A | 5/1953 | Cresswell | |
| 2,654,752 A | 10/1953 | Rhodehamel, Jr. et al. | 260/239.1 |
| 2,919,999 A | 1/1960 | Reissmann et al. | 106/161 |
| 2,920,000 A | 1/1960 | Hochstadt et al. | |
| 3,114,235 A | 12/1963 | Griset, Jr. | |
| 3,114,591 A | 12/1963 | Nichols et al. | |
| 3,114,593 A | 12/1963 | Griset et al. | |
| 3,157,524 A | 11/1964 | Artandi | |
| 3,293,237 A | 12/1966 | Wiegand | 260/123.7 |
| 3,366,440 A | 1/1968 | Nuwayser | 8/115.6 |
| 3,502,534 A | 3/1970 | Griset, Jr. | |
| 3,520,402 A | 7/1970 | Nichols et al. | |
| 3,587,586 A | 6/1971 | Kronenthal | 128/334 |
| 3,625,811 A | 12/1971 | Okamura | 162/2 |
| 3,742,955 A | 7/1973 | Battista et al. | 128/334 R |
| 3,810,472 A | 5/1974 | Aldinger | 128/287 |
| 3,823,212 A | 7/1974 | Chvapil | |
| 3,896,814 A | 7/1975 | Vivien et al. | 128/335.5 |
| 4,016,877 A | 4/1977 | Cruz, Jr. et al. | 128/156 |
| 4,066,083 A | 1/1978 | Ries | |
| 4,097,234 A | 6/1978 | Sohde et al. | |
| 4,140,537 A | 2/1979 | Luck et al. | 106/155 |
| 4,148,664 A * | 4/1979 | Cruz, Jr. | 604/368 |
| 4,193,813 A | 3/1980 | Chvapil | |
| 4,233,360 A | 11/1980 | Luck et al. | 428/310 |
| 4,238,480 A | 12/1980 | Sawyer | |
| 4,271,070 A | 6/1981 | Miyata et al. | 260/123.7 |
| 4,273,705 A | 6/1981 | Kato | 260/123.7 |
| 4,319,363 A | 3/1982 | Ketharanathan | 3/1.4 |
| 4,390,519 A | 6/1983 | Sawyer | 424/28 |
| 4,404,033 A | 9/1983 | Steffan | |
| 4,442,655 A | 4/1984 | Storetmann | 53/428 |
| 4,515,637 A | 5/1985 | Cioca | |
| 4,563,350 A | 1/1986 | Nathan et al. | 424/95 |
| 4,591,456 A | 5/1986 | Huc et al. | 530/356 |
| 4,760,131 A | 7/1988 | Sundsmo et al. | 530/356 |
| 4,863,732 A | 9/1989 | Nathan et al. | 424/95 |
| 4,880,429 A | 11/1989 | Stone | |
| 4,891,359 A | 1/1990 | Saferstein et al. | 514/21 |
| 4,894,441 A | 1/1990 | Menicagli | |
| 4,953,299 A | 9/1990 | Gimeno et al. | 34/92 |
| 4,963,146 A | 10/1990 | Li | |
| 4,980,403 A | 12/1990 | Bateman et al. | 524/17 |
| 5,028,695 A | 7/1991 | Eckmayer et al. | 530/356 |
| 5,124,438 A | 6/1992 | Brueckmann et al. | 530/354 |
| 5,219,576 A | 6/1993 | Chu et al. | 424/484 |
| 5,256,418 A | 10/1993 | Kemp et al. | |
| 5,274,078 A | 12/1993 | Wada et al. | 530/356 |
| 5,308,889 A | 5/1994 | Rhee et al. | |
| 5,331,092 A | 7/1994 | Huc et al. | 530/356 |
| 5,332,475 A * | 7/1994 | Mechanic | 204/157.68 |
| 5,378,469 A | 1/1995 | Kemp et al. | |
| 5,422,264 A | 6/1995 | Quaranta et al. | 535/240.2 |
| 5,562,946 A | 10/1996 | Fofonoff et al. | |
| 5,639,654 A | 6/1997 | Bernard et al. | 435/325 |
| 5,658,789 A | 8/1997 | Quraanta et al. | 435/375 |
| 5,667,961 A | 9/1997 | Bernard et al. | 435/1 |
| RE35,748 E | 3/1998 | Luck et al. | |
| 5,786,421 A | 7/1998 | Rhee et al. | 525/54.1 |
| 5,800,372 A | 9/1998 | Bell et al. | 602/48 |
| 5,874,537 A | 2/1999 | Kelman et al. | 530/356 |
| 5,972,366 A * | 10/1999 | Hayes et al. | 424/422 |
| 5,997,895 A | 12/1999 | Noratam | |

OTHER PUBLICATIONS

Cavallaro et al., "Collagen Fabrics as Biomaterials," *Biotechnology and Bioengineering*, (1994) vol. 43, pp. 781–791.

Mancini et al., "A Technique for the Prevention of Automatic Implantable Cardioverter Defibrillator Generator Migration," *Pace* (1990), vol. 13, pp. 946–947.

"Biologically Active Collagen Fibers and Fibrous Materials," *Khim. Volokna*, (1990), vol. 6, pp. 39–41—English Translation provided—(pp. 1–5).

Liening E, et al., "A Comparison of the Biocompatibility of Three Absorbable Hemostatic Agents in the Rat Middle Ear," *Otolaryngol Head Neck Surg.* (1997) 116:454–457.

Green J., et al., "Application of INSTAT Hemostat in the Control of Gingival Hemorrhage in the Patient with Thrombocytopenia," *Oral Surg. Oral Med. Oral Pathol.*, (1991) 71:27–30.

Wagner, W., et al., "Comparitive in Vitro Analysis of Topical Hemostatic Agents," *Journal of Surgical Research*, (1996) 66:100–108.

Johnson & Johnson Product Insert on Web Page for Instat® collagen absorbable hemostat (nine pages).

* cited by examiner

COLLAGEN HEMOSTATIC FIBERS

FIELD OF THE INVENTION

This invention relates to the field of hemostatic devices for controlling bleeding.

BACKGROUND OF THE INVENTION

Uncontrolled bleeding can result in shock and death. In surgical patients and patients receiving anticoagulant medication, the problem of rapid blood loss arising from, for example, a hemorrhage of a blood vessel, body tissue, organ or bone can give rise to a life threatening situation.

Biodegradable devices for controlling bleeding are commercially available. However, many of these devices require the impregnation of protein agents such as thrombin or fibrinogen to be effective. Unfortunately, special storage conditions are required to preserve the hemostatic activity of these protein agents. For example, many of these devices must be stored under refrigeration conditions to maintain the bioactivity of the hemostatic devices into which the protein agents have been impregnated. Such requirements prohibit certain field applications of the device, where refrigeration facilities are unavailable. Another problem with certain commercially available hemostatic devices is their lack of flexibility in the dry state. Many hemostatic devices do not conform easily to the shape of the body surface to which it is applied. In addition, hemostatic devices which further include hemostatic agents, such as thrombin, typically require that the thrombin be reconstituted and added to the dry devices immediately before use to provide a flexible hemostatic device having sufficient hemostatic activity to control bleeding.

SUMMARY OF THE INVENTION

The invention provides a hemostatic collagen fiber which can be processed into a hemostatic fabric. The collagen fibers and hemostatic fabric of the invention are collectively referred to herein as "hemostatic devices". The hemostatic devices of the invention solve the above-described and other problems of the prior art hemostatic fibers and fabrics. For example, the hemostatic devices of the invention do not require exogenously added protein agents to be effective. Accordingly, the hemostatic devices of the invention can withstand elevated temperatures and do not require refrigeration to retain hemostatic efficacy. In addition, the hemostatic fabrics of the invention are easy to use and mold easily to body contours. Accordingly, the hemostatic fabrics of the invention are particularly useful for treating the problematic hemorrhages of parenchymal organs, spine and brain.

According to one aspect of the invention, a hemostatic collagen fiber is provided. Hemostasis is a term of art which refers to cessation of bleeding. The collagen fiber contains collagen particles (preferably, collagen fibrils) which, preferably, have a hemostatic activity that is equivalent to the hemostatic activity of the collagen fibrils from which the fiber is formed. In the preferred embodiments, the fiber is prepared by a process which involves extruding a collagen slurry containing collagen fibrils into a dehydrating bath. An exemplary process is summarized below and described in detail in the Examples.

In one embodiment of the invention, the method for forming a collagen fiber of the invention involves suspending a plurality of collagen particles (preferably, collagen fibrils) in water to form a collagen slurry. The collagen fibrils have a bulk density sufficient to form a suspension in water. In general, the bulk density of the collagen fibrils is in the range of from about 1.5 to about 3.5 $lbs/ft^3$ and, more preferably, from about 2 to about 3 $lbs/ft^3$. The fibrils are suspended in water to obtain a collagen concentration in the range of about 3% to about 10% (weight/volume). Preferably, the collagen fibrils of the fiber have a hemostatic activity that is equivalent to the hemostatic activity of the collagen fibrils from which the fiber is formed. In the preferred embodiments, the collagen fibers are formed of collagen fibrils that have not been subjected to acid dissolution or other denaturing conditions.

According to the foregoing embodiment, the collagen slurry is introduced into a first dehydrating bath to at least partially dehydrate the collagen slurry and, thereby, form a collagen fiber. The collagen fiber, optionally, is introduced into a second dehydrating bath to further dehydrate the fiber. Exemplary dehydrating baths that can be independently selected for use as the first or second (if present) dehydrating baths include (1) an ammonia bath comprising from about 10% to about 30% ammonia in water; (2) an ammonia/acetone bath comprising from about 50% to about 70% ammonia in acetone; (3) an acetone bath; (4) an ethanol bath; (5) an isopropanol bath (containing about 70% isopropanol in water); and (6) a propylene glycol bath (containing about 30% to about 95% propylene glycol in water).

Preferably, the first dehydrating bath is an ammonia bath and the second dehydrating bath is an acetone bath.

According to yet another aspect of the invention, a collagen fiber prepared by the above-described process is provided. According to yet another aspect of the invention, a collagen fabric formed of the collagen fibers of the invention and methods of preparing the collagen fabrics are provided. Such fabrics are also referred to herein as "hemostatic fabrics" of the invention.

The collagen fibers and hemostatic fabrics of the invention are referred to herein as "hemostatic devices" of the invention. Such hemostatic devices can be sterilized and packaged in a sterile package for pharmaceutical applications.

In certain embodiments, the hemostatic devices of the invention further include a hemostasis-promoting amount of at least one hemostatic agent. As used herein, a "hemostasis-promoting amount" is the amount effective to accelerate clot formation at an interface between a surface (e.g., of a wound or lesion) and the hemostatic fabric. Exemplary hemostatic agents include a thrombin molecule, a fibrinogen molecule, a source of calcium ions, an RGD peptide, protamine sulfate, an epsilon amino caproic acid, and chitin. In the preferred embodiments, the hemostatic agent is thrombin. The hemostatic agents can be introduced into the hemostatic devices at any stage during the preparation of these devices.

In certain embodiments, the hemostatic devices of the invention further include a therapeutically effective amount of at least one therapeutic agent, such as agents which promote wound-healing and or reduce pain (e.g., vascular pain). Agents which promote wound-healing and/or reduce pain include anti-inflammatory agents (steroidal and non-steroidal) such as agents which inhibit leukocyte migration into the area of surgical injury, anti-histamines; agents which inhibit free radical formation; and bacteriostatic or bacteriocidal agents.

Various additives, optionally, can be incorporated into the hemostatic devices of the invention without adversely affecting the hemostatic activity of these devices. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the collagen fibrils of the present invention, and with each other, in a manner such that there is no interaction which would substantially impair the desired hemostatic activity.

The hemostatic devices of the invention are useful for promoting hemostasis at a site of bleeding (e.g., reducing or eliminating bleeding from a wound). Accordingly, a further aspect of the invention involves a method for promoting hemostasis. In general, such methods of the invention involve manually pressing a hemostatic fabric formed of the collagen fibers of the invention against a surface of a wound or a surface of a lesion on an organ, such as a parenchymal organ (e.g., spleen, liver, lung or pancreas), the spine, or the brain, for a period of time until clotting has occurred at the interface between the hemostatic fabric and the surface.

According to yet another aspect of the invention, a collagen fiber is provided, wherein the collagen fibrils of the fiber have a hemostatic activity that is equivalent to the hemostatic activity of the collagen fibrils from which the fiber is formed. Hemostatic fabrics formed of such collagen fibers also are provided. Although not wishing to be bound to any particular theory or mechanism, it is believed that avoiding contact between the collagen and an acid solution and minimizing exposure of the collagen to a denaturing condition such as, e.g., excess mechanical shear, high temperature, or long water residence times, during the fiber- or fabric-forming process results in a greater retention of hemostatic activity by the collagen.

A number of embodiments of the invention are summarized above. However, it should be understood that the various limitations presented in each embodiment are not mutually exclusive and, accordingly, the limitations can be combined to obtain further aspects of the invention.

DETAILED DESCRIPTION OF THE PREFERRED EMBODIMENTS

Figure 1:
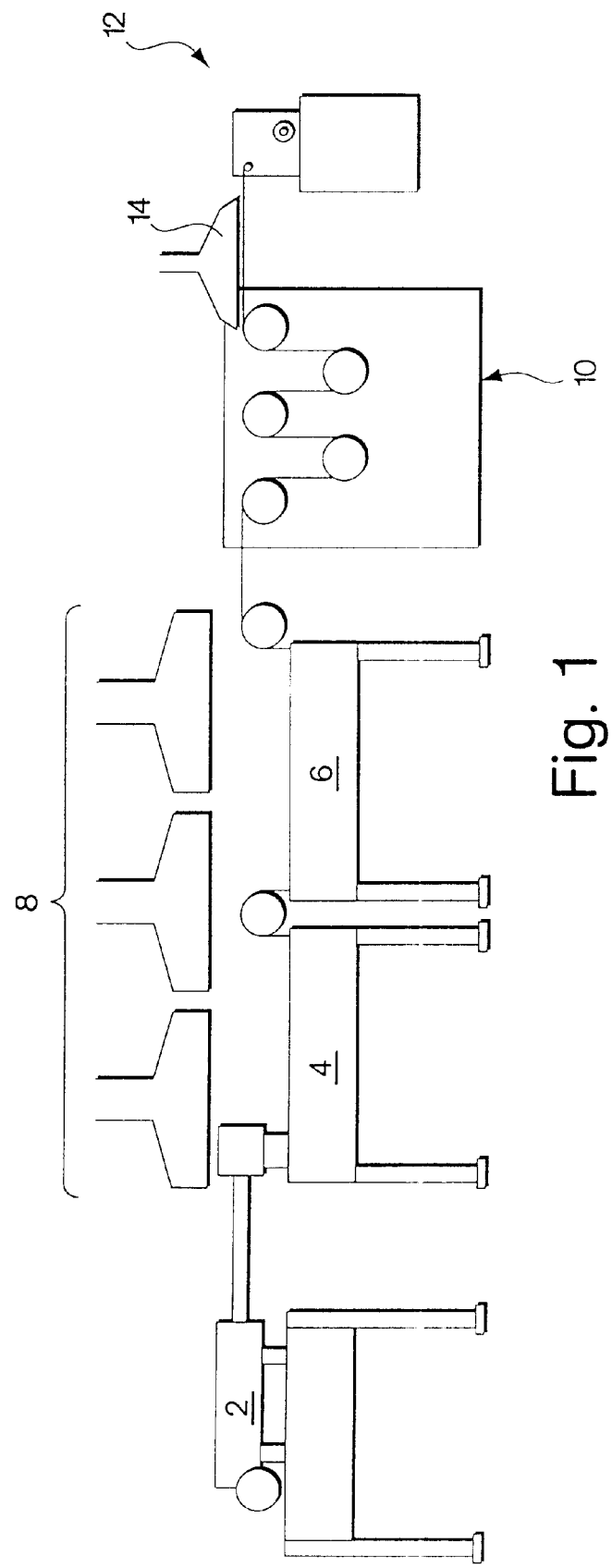
FIG. 1 illustrates a process for forming a collagen fiber in accordance with the invention.

According to one aspect of the invention, a collagen fiber having hemostatic activity is provided. The collagen fiber of the invention comprises a biodegradable fiber formed of a collagen, such as a microfibrillar collagen (e.g., absorbable Avitene® flour), which has not been subjected to acid dissolution or exposed to denaturing conditions. The collagen fibers in the invention possess a hemostatic activity. Although applicants do not wish to be bound to one particular theory or mechanism, it is believe that avoiding contact of the collagen with acid solution and minimizing exposure of the collagen to denaturation steps prior to and during the fiber-and-fabric-forming process, results in a greater retention of the hemostatic activity by the collagen starting material. In a preferred embodiment, the collagen fiber of the invention is formed of Avitene® flour which has not been subjected to acid dissolution or exposed to denaturing conditions, such as, e.g., excess mechanical shear, high temperatures or long water residence times. Accordingly, the invention provides a hemostatic devices having unexpected improved hemostatic properties compared to the hemostatic devices of the prior art that are formed by processes which involve collagen dissolution in acid solution or exposure to denaturing conditions.

According to one aspect of the invention, a method for forming a collagen fiber of the invention is provided. The method involves: (a) suspending a plurality of collagen particles (preferably, collagen fibrils) in water to form a "collagen slurry", wherein the collagen fibrils have a bulk density sufficient to form a suspension in water (preferably, in the range of from about 1.5 to about 3.5 lbs/ft$^3$) and wherein the collagen slurry has a collagen concentration in the range of about 3% to about 10% (weight/volume); and (b) introducing the collagen slurry into a first dehydrating bath to at least partially dehydrate the collagen slurry and thereby form a collagen fiber. In certain preferred embodiments, the collagen fibrils that are used to form the collagen fibers of the invention have a bulk density in the range of from about 2 to about 3 lbs/ft$^3$. In these and other certain preferred embodiments, the collagen slurry has a collagen concentration in the range of about 5% to about 8% (weight/volume).

In general, it is preferred that the process includes the further step of degassing the collagen slurry prior to extruding the slurring into the first dehydrating bath. The process can be accomplished on a relatively small scale by employing a syringe as an extruder. For example, the collagen slurry can be placed into a syringe (e.g., 5 to 60 cc) which is used an "extruder" for extruding the slurring into a dehydrating bath. A stopper is placed on the luer-lock end and the syringe is placed into a centrifuge. The "slurry" preferably is centrifuged to remove excess air bubbles (de-gas). The syringe is then placed onto a screw driven syringe pump with a needle of 14 to 40 gauge needle. Alternatively, the process can be accomplished on a larger scale and, optionally, automated, using the exemplary process illustrated in FIG. 2 and described in the Examples. According to this embodiment, an extruder (2) is used to deliver a controlled amount of collagen slurry at a controlled rate of speed to a first dehydrating bath (4) (e.g., an ammonia bath) and, optionally, a second dehydrating bath (6). In a preferred embodiment, the slurry is extruded into an ammonia bath and/or an ammonia/acetone bath at a rate of speed sufficient to form a collagen fiber in the dehydrating bath. Preferably, the process is performed in an environment which includes an exhaust system (8) to remove noxious vapors that may originate from the dehydrating baths. In the preferred process, a draw frame (14) and a take-up element (12) provide the mechanism by which the emerging collagen fiber is drawn through the process steps. Optionally, the process further includes a dryer (14) to provide a dried collagen fiber of the invention. Further examples of a process in which a collagen dispersion is extruded into a dehydrating bath or a coagulating bath to form a collagen fiber or ribbon are shown in Patent Nos. U.S. Pat. No. 3,114,593, entitled "Method of Producing a Collagen Strand", issued to Griset; U.S. Pat. No. 3,114,591, entitled "Process for the Manufacture of Suture Material from Animal Tendons", issued to Nichols et al.; U.S. Pat. No. 2,920,000, entitled "Collagen Article and the Manufacture Thereof", issued to Hochstadt et al.; U.S. Pat. No. 2,637,321, entitled "Shaped Article and Method of Producing It", issued to Cresswell; and U.S. Pat. No. 2,598,608, entitled "Preparation of Collagenous Materials", issued to Salo et al.

The process of the invention avoids dissolving the collagen in acid solution and minimizes or avoids exposing the collagen to other process steps which could denature the collagen and, thereby, adversely affect its hemostatic activity. In the preferred embodiments, the collagen is microfibrillar collagen; more preferably, a collagen flour such as Avitene® flour. Accordingly, in certain embodiments, the fibrils of the hemostatic devices of the invention have a hemostatic activity that is about the same as the hemostatic activity of Avitene® flour. Avitene® flour is a microfibrillar collagen hemostat that is indicated for all surgical specialties, including neurosurgery, vascular, orthopaedic, urologic, and other general procedures. Avitene® is available from Davol, Inc. (product numbers 101001, 101002, 101003, 101004, and 101034, Cranston, R.I.). The process for preparing Avitene® flour is described in U.S. Pat. No. 3,742,955, issued to Battista et al.

As used herein, "hemostatic activity" refers to the ability to stop bleeding and can be determined, e.g., in animal models that are recognized as predictive of an in vivo effect by those of ordinary skill in the art. Exemplary hemostasis animal models include the pig and dog spleen animal models. A preferred animal model for hemostasis activity is provided in the Examples.

Preferably the method for preparing the collagen fibers of the invention further includes the step of (c) introducing the collagen fiber into a second dehydrating bath. The first dehydrating bath and the second dehydrating bath (if present) are independently selected from the group consisting of: (1) an ammonia bath comprising from about 10% to about 30% ammonia in water; (2) an ammonia/acetone bath comprising from about 50% to about 70% ammonia in acetone; (3) an acetone bath; (4) an ethanol bath; (5) an isopropanol bath (containing about 70% isopropanol in water); and (6) a propylene glycol bath (containing about 30% to about 95% propylene glycol in water). Preferably, the first dehydrating bath is an ammonia bath and the second dehydrating bath is an acetone bath.

In certain embodiments, the fiber-forming processes described herein, optionally, further include the step of drying the collagen fiber. The collagen fibers, in wet or dry state, can be formed into hemostatic fabrics using conventional fiber-processing technology (e.g., weaving, knitting).

According to another aspect of the invention, the processes for forming the hemostatic devices of the invention further includes the step of introducing a hemostatic agent into the fiber or fabric. The hemostatic agent can be introduced into the collagen fiber or hemostatic fabric of the invention at any stage in the process, including before the fiber-formation step (e.g., by adding the hemostatic agent to the slurry) and after fabric formation step (e.g., by soaking the hemostatic fabric in a solution containing one or more hemostatic agents).

It is believed that the hemostatic fabrics of the invention do not require a hemostatic agent to function effectively to control bleeding, e.g., hemorrhage of a parenchymal organ. As a result, the hemostatic devices of the invention which do not further contain a hemostatic agent have good thermal stability and can be stored for months to a few years without refrigeration and losing effectiveness. Such embodiments of the invention are useful for various medical situations and are particularly useful for field and emergency use, since each may be stored in a ready-to-use state for a lengthy period, even in the absence of refrigeration.

Such devices of the invention also are less expensive to make and/or use compared to hemostatic devices which contain a further hemostatic agent to achieve a comparable level of hemostatic activity.

One advantage of the hemostatic fabric of the invention is its flexibility compared to hemostatic devices such as Gelfoam®, that is, the hemostatic fabrics of the invention can be provided in a form that easily conforms to the contours of an organ or biological surface, making the manipulation of applying the foam quicker to perform. As a result, there is less overall blood loss to the patient and less time is spent in surgery. Further, the hemostatic fabrics of the invention can be applied, in wet or dry state, to a bleeding site and do not require pre-wetting with a sterile solution prior to use.

The collagen fibers of the invention are formed of an absorbable collagen from any source, e.g., corium collagen, tendon collagen, and preferably is a microfibrillar collagen. More preferably, the fiber preferably is formed of a collagen flour, such as Avitene® flour. The fibers can be fabricated into hemostatic fabrics having predictable hemostatic activities, based on the activities of the collagen fibers of the invention. The effectiveness of fabrics of the present invention in promoting clot formation is further enhanced by their lattice structures, which are selected to be of a sufficient weave size to promote enzyme substrate interactions. In particular, the weave size and structure of the hemostatic fabrics of the invention are selected to enhance contact between thrombin that, optionally, is provided exogenously in the fabric with endogenous fibrinogen present in the blood exuding from a wound or lesion of, e.g., a parenchymal organ, a spine or a brain.

In certain embodiments, at least one hemostatic agent can be included in the hemostatic devices of the invention. Because certain combinations of hemostatic agents can act synergistically, the amount of each hemostatic agent can be less than that which would be required to improve the hemostatic activity of the hemostatic devices of the invention if the agents were used individually. Accordingly, the collective amount of the hemostatic agent(s) which are included in the collagen fiber or hemostatic fabric of the invention is a "hemostasis-promoting amount", i.e., the amount of at least one hemostatic agent effective to accelerate clot formation at an interface between a surface (e.g., of a wound, of a lesion on a parenchymal organ, the spine or the brain) and the hemostatic devices of the invention.

Exemplary hemostatic agents that can be applied to the hemostatic devices of the invention in amounts effective for stimulating hemostasis, include, but are not limited to: thrombin, an enzyme which converts fibrinogen to fibrin; calcium, sodium, magnesium or other ions that stimulate hemostasis; protamine sulfate, an epsilon amino caproic acid, fibrinogen, and chitin. Epsilon amino caproic acid and its analogs which possess a similar chemical structure and hemostatic activity for use in a hemostatic device are described in U.S. Pat. No. 5,645,849, assigned to Clarion Pharmaceuticals. In terms of ion additives, calcium chloride is generally a preferred additive for introducing a calcium ion into the foam.

Thrombin is an active ingredient found in other hemostatic devices. It is believed that, in general, the collagen fibrils of the hemostatic devices of the invention have a hemostatic activity that is equivalent to the hemostatic activity of the collagen fibrils from which the fiber is formed. Thus, the invention (without thrombin) advantageously provides a device having enhanced hemostatic activity compared to the hemostatic devices of the prior art. A further increase in the hemostatic activity of the hemostatic devices of the invention can be achieved by, optionally, including a hemostatic agent in the hemostatic devices of the invention.

As used herein, the term "equivalent" with respect to hemostatic activity means that the hemostatic activity is substantially the same when measured in the same activity assay. An exemplary hemostatic activity assay, a pig spleen hemostasis assay, is provided in the examples. The assay can be used to measure the hemostatic activity of the devices of the invention and can also be used to measure the hemostatic activity of the collagen particles, e.g., collagen flour, from which the hemostatic device is formed by, for example, by placing powder over the incision, overlaying the powder with a sterile gauze, and applying pressure to the wound in the same manner as described in the example for a device of the invention. The experimental results for the pig spleen assay are reported in terms of the number of tamponades necessary to achieve hemostasis at an incision in the pig spleen. The number of tamponades for multiple samples is determined to obtain a distribution of the number of tamponades. The distribution of tamponades is a measure of the hemostatic activity for the device or flour that is being tested. Accordingly, devices which have a similar distribution of tamponades have "equivalent" hemostatic activity. For example, if 80 of 100 samples of a first device require one tamponade to achieve hemostasis, and 70 of 100 samples of a second device require one tamponade to achieve hemostasis, the hemostatic activity of the second device is considered to be within 10% of the hemostatic activity of the first device. Equivalent hemostatic activity means that the hemostatic activity for two samples are within at least 50%, more preferably, within 60%, 70%, 80%, 90% and, most preferably, within 95%.

The preferred hemostatic agent is thrombin (e.g., human or bovine thrombin). Preferably, the thrombin is a recombinant thrombin to avoid viral or other contamination from the organism from which the thrombin is derived. The molecules "thrombin" and "fibrinogen", as defined herein, are meant to include natural thrombin and fibrinogen molecules derived from an animal or human origin, a synthetic form or a recombinant form of the molecules, including functionally active analogs that effectively maintain the enzyme's clot promoting activity in an animal or human. The species of animal from which the molecule is derived can vary and depends on the intended use of the foam. For example, a foam intended for human use for safety reasons preferably contains recombinant human thrombin or non-human thrombin, e.g., bovine thrombin. By avoiding use of human fibrinogen isolated from a human tissue or using viral deactivated human thrombin, risks associated with viral contamination of purified blood products are minimized.

Additionally or alternatively, the tripeptide RGD, composed of arginine, glycine and aspartic acid, and optionally serine "RGDS," can be incorporated into the hemostatic devices of the invention as a hemostatic agent. RGD is the active site of fibrinogen and fibronectin. RGD accelerates wound healing and is believed to stimulate fibroblast migration. The RGD additive is also much less expensive than fibrinogen because it can be synthesized using solid phase chemistry.

Thrombin-containing hemostatic devices of the inventions can be prepared in a variety of ways to result in fibers and fabrics in which the thrombin is dispersed within the hemostatic device or applied to a surface of the hemostatic device in an amount effective for inhibiting fibrinolysis and, thereby, stimulating clot formation. Thus, according to one embodiment, a hemostatic device of the invention is made by applying to the hemostatic device, an amount of thrombin effective for promoting (stimulating) hemostasis.

The hemostatic agent can be introduced into the hemostatic device of the invention at any stage in the process, including before the device-formation step (e.g., by adding the hemostatic agent to the slurry) and after device formation step (e.g., by soaking the hemostatic device in a solution containing one or more hemostatic agents). Thrombin and/or other hemostatic agents or additives described as components of a hemostatic device according to the invention, can be applied to the hemostatic device by any of several methods which all would be performed most advantageously under sterile conditions. Thrombin can be introduced into the collagen slurry prior to extrusion or applied as a layer to a particular surface or side of a hemostatic device of the invention, which surface is then designated as the wound-contacting surface. For example, this can be accomplished by spraying thrombin in powder form onto a hemostatic device of the invention. Alternatively, a solution of thrombin can be coated onto a hemostatic device of the invention and dried by lyophilization or by conventional means. In another method of applying thrombin, a hemostatic device of the invention is dipped completely or partially into a sterile solution of thrombin such that a sufficient amount of thrombin accumulates within the hemostatic device effective to inhibit fibrinolysis in a mammal. Preferably, the thrombin solution contains 1000 I/U of thrombin dissolved in I ml saline. The amount of thrombin applied in the solution can vary. Preferably, the total amount of thrombin applied to a hemostatic device of the invention or surface thereof is 100–1000 units/cm$^3$. It is understood that alternative methods of applying the hemostatic agents and additives to a hemostatic device of the invention in addition to the methods described herein also can be used.

The collagen fiber or hemostatic fabrics of the invention that have been soaked in thrombin solution or other solution containing a hemostatic agent optionally can be dried. The drying step can be accomplished by lyophilization, preferably. Other drying procedures appropriate for a material containing an active protein ingredient can also be employed, so long as the drying treatment does not denature the proteins or render them inactive. Alternatively, the fiber or fabric can be dried by maintaining it at room temperature for a period of 1–3 hours, followed by refrigeration overnight.

In yet other embodiments, hemostatic agents other than, or in addition to, thrombin can be incorporated, partially or fully, into the hemostatic devices of the invention. For example, protamine sulfate can be added to the hemostatic devices of the invention in an amount that is effective to neutralize heparin in the local environment of the device. Protamine sulfate can be added in an amount between about 1–15 mg/cm$^2$ of the hemostatic device, preferably in an amount between 2–5 mg/cm$^2$ of a wound contacting surface of the hemostatic device.

Likewise, RGD or RGDS peptide can be dissolved in double distilled water and sprayed onto a wound-contacting surface of a hemostatic device of the invention. Preferably, such embodiments of the invention contain an amount of RGD effective to enhance clot formation. For example, RGD or RGDS can be applied to a hemostatic device of the invention in an amount between about 110130 mg/cm$^2$. Thus, a standard size hemostatic device that is a fabric would contain about 1–10 mg/fabric or about 5–7 mg/fabric of RGD or RGDS.

The hemostatic agents described herein can be applied to a fabric as a layer, for example, by spraying them onto the wound-contacting surface of the fabric in dry forms. Alternatively, the hemostatic fabrics of the inventions of the invention can be soaked in a solution containing the hemostatic agent. Accordingly, the invention embraces hemostatic fabrics of the inventions in which the hemostatic agent(s) are absorbed into the interstices of the fabric, as well as fabrics in which such agents are layered on a surface of the fabric. In certain embodiments, the hemostatic agents and additives are coated on only one surface (the wound-contacting surface) to minimize the likelihood of hemostasis between the wound and a non-wounded tissue in the vicinity of the fabric. In yet other embodiments intended for packing a void in body tissue, the fabric can be coated with hemostatic agent(s)on all surfaces.

In certain embodiments, the hemostatic devices of the invention further include a therapeutically effective amount of at least one therapeutic agent, such as agents which Is promote wound-healing and or reduce pain (e.g., vascular pain). Agents which promote wound-healing and/or reduce pain include anti-inflammatory agents (steroidal and nonsteroidal) such as agents which inhibit leukocyte migration into the area of surgical injury, anti-histamines; agents which inhibit free radical formation; and bacteriostatic or bacteriocidal agents. In general, a therapeutically effective amount means that amount necessary to delay the onset of, inhibit the progression of, or halt altogether the particular condition being treated. Generally, a therapeutically effective amount will vary with the subject's age, condition, and sex, as well as the nature and extent of the condition in the subject, all of which can be determined by one of ordinary skill in the art. The dosage of therapeutic agent contained in the hemostatic devices of the invention may be adjusted to accommodate the particular subject and condition being treated.

As used herein, the phrase, "agents which promote wound-healing" refers to agents, the administration of which, promote the natural healing process of a wound. Agents that promote wound-healing include anti-inflammatory agents, agents which inhibit free radical formation, and bacteriostatic or bacteriocidal agents.

Anti-inflammatory agents are agents which inhibit or prevent an immune response in vivo and include: (i) agents which inhibit leukocyte migration into the area of surgical injury ("leukocyte migration preventing agents"), and anti-histamines. Representative leukocyte migration preventing agents include silver sulfadiazine, acetylsalicylic acid, indomethacin, and Nafazatrom. Representative anti-histamines include pyrilamine, chlorpheniramine, tetrahydrozoline, antazoline, and other anti-inflammatories such as cortisone, hydrocortisone, beta-methasone, dexamethasone, fluocortolone, prednisolone, triamcinolone, indomethacin, sulindac, its salts and its corresponding sulfide, and the like.

Representative agents which inhibit free radical formation include antioxidants that inhibit the formation and/or action of oxide products, superoxide dismutase (SOD), catalase, glutathione peroxidase, b-carotene, ascorbic acid, transferring, ferritin, ceruloplasmin, and desferrioxamine α-tocophenol.

Representative bacteriostatic or bacteriocidal agents include antibacterial substances such as β-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentarnycin, kanamycin, amikacin, sisomicin and tobramycin; nalidixic acids and analogs such as norfloxican and the antimicrobial combination of fluoroalanine/pentizidone; nitrofurazones, and the like.

The hemostatic devices of the invention can contain one or more therapeutic agents, alone or in combination with one or more hemostatic agents.

Various additives, optionally, can be incorporated into the hemostatic devices of the invention without adversely affecting the hemostatic activity of these devices. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the collagen fibrils of the present invention, and with each other, in a manner such that there is no interaction which would substantially impair the desired hemostatic activity.

According to certain embodiments, a hemostatic device of the invention is contained within a sealed sterile package which facilitates removal of the hemostatic device without contamination. Such a package, for example, can be an aluminum foil pouch or other material that is easily sterilized. Radiation, e.g., gamma radiation, can be applied to sterilize the hemostatic device and packaging material together. In yet other embodiments, a container having dual compartments is provided in which a first compartment contains distilled water, sterile saline or a sterile buffer, and a second compartment contains a hemostatic device of the invention. The hemostatic device of the second compartment can be readily dipped into an opened first compartment and subsequently applied to the wound.

According to yet another aspect of the invention, a product prepared by the above-described process is provided. A particular embodiment of this process in provided in the Examples. The process, optionally, further includes the step of cross linking the collagen within the hemostatic devices of the invention, e.g., by heating the collagen fibers of the invention at a temperature and for a period of time sufficient to form crosslinks without adversely affecting the hemostatic activity of the collagen fiber.

According to still another aspect of the invention, a method for promoting hemostasis is provided. The method involves the steps of pressing a hemostatic fabric of the invention against a surface of a wound or a surface of a lesion on an organ, tissue, or other bleeding surface, e.g., a parenchymal organ, the spine or the brain, for a period of time until clotting has occurred at the interface between the hemostatic fabric of the invention and the surface. The fabric may be applied to the surface in a dry state or, alternatively, may be soaked in sterile saline solution or a sterile hemostatic agent-containing solution prior to use. Use of a hemostatic fabric of the invention according to the invention, without first soaking in saline solution permits quick and simple application of the fabric in various situations, including field situations such as may be encountered by an emergency medical technician. In certain embodiments, the hemostatic fabric is soaked in a thrombin solution prior to use to introduce a therapeutically effective amount of thrombin into the sponge. Thus, a collagen fabric of the invention of the invention can be used by applying a "wound-contacting" surface of the fabric, a surface intended to contact the wound and containing hemostatic agent(s) and, optionally, additives, with or without prior soaking in a sterile solution, to a surface of a bleeding wound or lesion. Then, the fabric is maintained in contact with the surface for a period of time sufficient for clotting to occur at the interface between the hemostatic fabric of the invention and the surface and for bleeding to be substantially arrested. Preferably, the fabric is maintained in contact with the surface for a period of about 3–20 minutes, advantageously 3–10 minutes, and more advantageously, 3–5 minutes.

Where thrombin and/or other hemostatic agents also are present on/in the hemostatic fabric, the time period is preferably about 5 minutes. The hemostatic fabric is held in place against the biological surface, preferably with light pressure, e.g., by means of a sterile saline soaked sponge. Alternatively, the hemostatic fabric may be held in place simply by applying pressure to the hemostatic fabric by means of a gauze or other dry sterile material. Depending on the location of the wound, a bandage can be wrapped around the hemostatic fabric to provide light pressure on the wound surface.

The efficacy of the hemostatic fabrics of the invention can be assessed in art-recognized animal models that are believed to be predictive of an in vivo hemostatic effect in humans. For example, surgical lesions induced in parenchymal organs of pigs provide a good model system for hemostasis in the analogous human organs as evidenced by preclinical studies which employ pig models. See e.g., SWINE AS MODELS IN BIOMEDICAL RESEARCH, Swindle, M., Iowa State Univ. Press (1992).

A preferred use of a hemostatic fabric according to the present invention is to inhibit or completely stop bleeding of a parenchymal organ, such as the liver, kidney, spleen, pancreas or lungs. Other preferred uses are to inhibit or completely stop bleeding of a wound or lesion on the spine or brain. Additional uses for the hemostatic fabrics of the invention include inhibiting bleeding during surgery, e.g., internal/abdominal, vascular (particularly for anastomosis), urological, gynecological, thyroidal, neurological, tissue transplant uses, dental, cardiovascular, cardiothoracic, ENT (ear, nose, throat), and orthopedic surgeries.

Another use of a hemostatic fabrics of the invention is topical treatment, such as for burn or tissue transplants or dura replacement and/or substitution. A hemostatic fabric of the invention for topical use preferably contains additives, such as anti-infection medicaments, bactericides, fungicides and wound healing agents, for example, neomycin and bacitracin.

In addition to inducing hemostasis, the hemostatic fabrics of the inventions of the invention can be used to hermetically sealing body tissue. For example, when air leaks from a wound in the lungs, a hemostatic fabric of the invention can be applied to the surface surrounding the wound, held in place for a period of time sufficient to induce hemostasis and allow a hermetic seal to form.

The hemostatic devices of the invention also are useful for treating animals, preferably humans or other mammals, including domestic mammals and livestock.

The hemostatic fabrics of the invention can be provided in a variety of sizes and shapes, depending upon its intended use. Typically, the hemostatic fabrics of the invention are provided in a standard size rectangular fabric, e.g., 2"×14"; 1"×1"; 4"×8"; 1"×3.5"; 2"×3"; 3"×4"; 0.5"×2"; and 6"×9". The hemostatic fabrics may be cut to size with a pair of scissors. The hemostatic fabrics of the invention may be folded, bundled, wrapped, or prefabricated into small squares, such as for packing into a body cavity, such as a dental cavity following a tooth extraction. The collagen fibers of the invention may be knitted into various structures. Alternatively, the hemostatic fabric can be shaped for epistaxis (profusely bleeding nostril) or insertion into a cavity. The hemostatic fabrics of the invention that are intended for topical applications can be applied with an adhesive tape, as a band-aid form, where the hemostatic fabric is adhered to an adhesive backing. One or more additional layers of wound dressing material, preferably a layer which aids in absorption of blood or other exudants, can be applied to or incorporated into the hemostatic fabrics of the invention to form a stronger bandage. Alternatively, the layer may be applied as a supplement to the backside (non-wound contacting surface) of a fabric according to the invention. Particularly for topical use, the layer(s) can contain superabsorbents to wick exudant solution from the wound site. For hemostatic fabrics of the inventions intended for internal-surgical applications, where an added layer(s) is integral with the fabric, the layer(s) should be both biodegradable and pharmaceutically acceptable.

The hemostatic fabrics of the invention can designed to facilitate its application to fuse ends of a blood vessel or other body lumen having been severed, e.g., surgically. To apply a hemostatic fabric for anastomosis, a rectangular fabric, for example, is wrapped around the external surface of the ends of a Dacron® graft and the graft is positioned into place. The hemostatic fabric portion of the graft accelerates fibrin growth into the graft to seal the graft in place (hemostatically and hermetically). According to certain embodiments of the invention, a kit is provided for this application. The kit contains a graft and a hemostatic fabric of the invention that is designed for fitting with the ends of the graft. Alternatively, a kit is provided having a hemostatic fabric of the invention pre-fitted onto at least one end of a graft.

According to still other aspects of the invention, various specialized kits can be provided. The kits contain any of the hemostatic device embodiments disclosed herein and a package, wherein the hemostatic device of the invention is contained within a sealed sterile package which facilitates removal of the fabric without contamination. The kit can contain multiple hemostatic devices of the inventions, preferably wherein each hemostatic device is contained within a separate sealed sterile package. A kit that is designed for autonomous use, e.g., for field/military use can, in addition to a hemostatic fabric of the invention, further include disposable pre-sterilized surgical instruments and/or agents that can be incorporated into the fabric, e.g., thrombin, calcium chloride.

Unless defined otherwise, all technical and scientific terms used herein have the same meaning as commonly understood by one of ordinary skill in the art of the invention. Although any methods and materials similar or equivalent to those described herein can be used in the practice of the invention, the preferred methods and materials have been described. Unless mentioned otherwise, the techniques employed or contemplated herein are standard methodologies well known to one of ordinary skill in the art. The materials, methods and examples are illustrative only and not limiting.

EXAMPLES

Example 1

PREPARATION OF A COLLAGEN FIBER FROM A COLLAGEN SLURRY

Avitene® flour (microfibrillar collagen) is mixed with water at about a 2 to 10% mixture (by weight to volume) with optimum being 5% and allowed to swell in water for a 4 to 72 hour period. Avitene® flour is available from Davol, Inc. (product numbers 101001, 101002, 101003, 101004, and 101034, Cranston, R.I.). The "slurry" (collagen swelled by water) is filled into a syringe of 5 to 60 cc. A stopper is placed on the luer-lock end and the syringe is placed into a centrifuge. The "slurry" is centrifuged to remove excess air bubbles (de-gas). The syringe is then placed onto a screw driven syringe pump with a needle of 14 to 40 gauge needle. The slurry is extruded into an ammonia bath and/or an ammonia/acetone bath. In one embodiment, the bath is sixteen feet long to mildly dehydrate the fiber. The fiber is then further dehydrated in an acetone bath before being dried in a dynamic drying oven. The fiber is wound onto a spool in accordance with conventional procedures, using conventional equipment and further processed into a knitted or woven fabric. The fiber can be coated with a 20% glycerin and ethanol coating solution to aid the fibers in further processing knitting or weaving).

Optionally, the "slurry" can be homogenized and/or filtered to remove any fibrils or impurities that may cause defects in the fibers. The fibers can be either mono- or multi filament.

The collagen fibers of the invention are processed into a hemostatic fabric of the invention in accordance with standard procedures for forming a fabric, e.g., quilting or weaving. (See, e.g., Patent Nos. U.S. Pat. No. 3,114,593; U.S. Pat. No. 3,114,591; U.S. Pat. No. 2,920,000; U.S. Pat. No. 2,637,321; U.S. Pat. No. 2,598,608 (noted above), as well as U.S. Pat. No. 5,378,469, entitled "Collagen Threads"; U.S. Pat. No. 5,256,418, entitled "Collagen Constructs"; PCT/US92/08520, entitled "Collagen Constructs" (publication no. WO 93/06791, priority claimed to U.S. Ser. No. 772,529, now U.S. Pat. No. 5,378,469); PCT/US95/03455, entitled "Three-dimensional Bioremodelable Collagen Fabrics" (publication no. WO 95125482, priority claimed to U.S. Ser. No. 08/215,760); and PCT/US95/03525, entitled "Biocompatible Prosthetic Devices" (publication no. WO 95/25550, priority claimed to U.S. Ser. No. 08/216,527).)

The hemostatic fabrics of the invention are intended for use as an adjunct for hemostasis. The process for forming Avitene flour involves swelling collagen in acidified alcohol, but does not involve acid dissolution of collagen. It is believed that the avoidance of acid dissolution in the Avitene® flour fabrication process is responsible for its enhanced hemostatic activity. Because the process for forming the Avitene® flour into fibers and then interlacing the fibers into a fabric also does not involve contacting the collagen with acid or exposing the collagen to other denaturing conditions, it is believed that the hemostatic fabrics of the invention exhibit enhanced hemostatic properties compared to known collagen fabrics.

Example 2
AUTOMATED PROCESS FOR PREPARATION OF A COLLAGEN FIBER

The following procedure is contemplated for automating the process for preparation of a collagen fiber. The procedure illustrative and is not intended to limit the invention in any way.

Mixing/Centrifuge of Slurry:

The collagen slurry is mixed at a concentration of about 3 to 10% w/v of Avitene Powder to water. The mixture is passed through a continual operation of a Horizontal Shaft Model D-8 Stainless Steel Versator (The Cornell Machine company, Springfield, N.J.), thereby eliminating the need to manual mix the slurry. The slurry can immediately be fed into the extruder for extrusion or it can be stored up to 72 hours before being extruded.

Extruder:

The collagen slurry is fed into the extruder feed throat and extruded at room temperature to about 50° C. through a ¾" diameter barrel with a 25:1 L/D ratio, air cooled extruder with a 2:1 compression ratio screw (C.W. Brabender Instrument, Inc., Hackensack, N.J.). The slurry passes through the barrel into the block with a metering pump assembly (0.6 to 1.2 ml/min.), which forces the slurry through the die assembly at a constant rate. The slurry can be extruded through a single hole die to a multifilament die of 30 holes.

Troughs (Dehydration Baths):

The slurry exits the die and enters the first dehydration bath (10 to 15 feet long×5 inches wide×5 inches deep, stainless steel) containing the first dehydration agent (preferably ammonia). The fiber(s) then passes into the second dehydration bath (5 feet long×5 inches wide×5 inches deep, stainless steel) containing the second dehydrating agent (preferably acetone). The baths are from C.W. Brabender Instruments, Inc., Hackensack, N.J.

Draw/Drying Frame:

The fiber(s) are wound through a draw frame (Dienes Laboratory Draw Winder—Single Position, Comoli DWI-2000, Dienes Apparatus, Inc., Pineville, N.C.) containing heated rollers to aid in the drying of the fiber while it is being drawn to specification of mechanical strength. The fiber can then be further dried (if necessary) by passing by a "hot gun" (blow dryer).

Winder:

The fiber(s) are then collected onto a spool (preferably perforated stainless steel), which is being spun by a winder (Leesona Style 50 Winder, Standard Mill Machinery Corp., West Warwick, R.I.).

Knitter:

The spool(s) of fiber can then be twisted together to form a multifilament or a single filament end can be used to form a fabric using a knitting machine (Circular Weft Knitting Machine, Lamb Knitting Machine Corp., Chicopee, Mass.).

Example 3
PROTOCOL FOR COMPARISON BETWEEN A HEMOSTATIC FABRIC OF THE INVENTION AND SURGICEL®

The following procedure is contemplated for comparing the hemostatic activity of a fabric of the invention and a representative, commercially available fabric. The procedure illustrative and is not intended to limit the invention in any way.

Hemostatic Activity Assay

The hemostatic fabrics of the invention contain Avitene® flour and water. The hemostatic response time of a sample hemostatic fabric of the invention ("TEST SAMPLE") with and without thrombin, is compared to Surgicel® (Johnson & Johnson Medical Inc., Arlington, Tex., with and without thrombin) in a pig spleen model (J&J Hemostasis protocol) as described below. Small incisions are made in the retracted spleen of anesthetized juvenile Yorkshire pigs. The number of cuts per spleen ranges from 8 to 18. Eight pigs are required. Thrombin is added by soaking the sample (TEST SAMPLE or Surgicel® sample) in a thrombin solution until fully saturated. The test article (approximately 0.5"×0.5") is placed on the wound, tamponaded with finger pressure for 20 seconds, then the pressure is removed and the site is observed for re-bleed for two minutes. If re-bleed is observed within two minutes, pressure is reapplied for 20 seconds and the cycle is repeated. The endpoint is the number of tamponades to achieve no re-bleed. The following samples are paired during testing (20 pairs each): TEST SAMPLE versus Surgicel®, TEST SAMPLE versus -Surgicel® thrombin, TEST SAMPLE-thrombin versus Surgicel® -thrombin. A pair is defined as two samples tested one after the other and adjacent to one another on the spleen. For each pair, the first sample tested is alternated from pair to pair. Each pair is tested at least once, usually twice, and sometimes 3 times on each animal to better characterize animal to animal variability.

The frequency of the number of tamponades for each product type within the paired group, is analyzed using the Fisher's exact test and The Stuart-Maxwell test (both one-tailed) at alpha 0.05. These paired groups are analyzed separately. Therefore, a one-sided test based on expected results is appropriate.

It is expected that TEST SAMPLE without thrombin would need fewer tamponades than Surgicel® with or without thrombin because the collagen in the TEST SAMPLE has not been subjected to acid dissolution or exposed to other denaturing conditions. Accordingly, it is believed that clinical users may choose to use the hemostatic fabrics of the invention in the dry state without thrombin, saving time and money, since only one product would be used instead of two. The soft and flexible handling characteristics of the hemostatic fabrics of the invention will allow it to be used in the dry state.

All of the references, patents and patent publications identified or cited herein are incorporated, in their entirety, by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed:

1. A method for forming a collagen fiber comprising:
   (a) suspending a plurality of collagen fibrils in water to form a collagen slurry, wherein the collagen fibrils have a bulk density sufficient to form a suspension in water and wherein the collagen slurry has a collagen concentration in the range of about 2% to about 10% (weight/volume); and
   (b) introducing the collagen slurry into a first dehydrating bath to at least partially dehydrate the collagen slurry and thereby form a collagen fiber.

2. The method of claim 1, wherein the collagen fibrils comprise microfibrillar collagen fibrils.

3. The method of claim 1, wherein the collagen fibrils comprise a collagen flour.

4. The method of claim 1, wherein the collagen fibrils have a bulk density in the range of from about 1.5 to about 3.5 lbs/ft$^3$.

5. The method of claim 1, wherein the collagen slurry has a collagen concentration in the range of about 5% to about 8% (weight/volume).

6. The method of claim 1, further comprising the step of
   (c) introducing the collagen fiber into a second dehydrating bath.

7. The method of claim 6, wherein the first dehydrating bath is an ammonia bath and the second dehydrating bath is an ammonia/acetone bath.

8. The method of claim 1, further comprising the step of drying the collagen fiber.

9. The method of claim 8, further comprising the step of drying the collagen fiber.

10. The method of claim 1, further comprising the step of forming the collagen fiber into a hemostatic fabric.

11. The method of claim 1, further comprising the step of degassing the collagen slurry prior to forming the collagen fiber.

12. The method of claim 1, comprising the further step of introducing a hemostatic agent into the fiber.

13. The method of claim 1, comprising the further step of introducing a therapeutic agent into the fiber.

14. A collagen fiber prepared by the process comprising:
   (a) suspending a plurality of collagen fibrils in water to form a collagen slurry, wherein the collagen fibrils have a bulk density sufficient to form a suspension in water and wherein the collagen slurry has a collagen concentration in the range of about 2% to about 10% (weight/volume); and
   (b) introducing the collagen slurry into a first dehydrating bath to at least partially dehydrate the collagen slurry and thereby form a collagen fiber.

15. The product of claim 14, wherein the collagen fibrils comprise microfibrillar collagen fibrils.

16. The product of claim 14, wherein the collagen fibrils comprise a collagen flour.

17. The product of claim 14, wherein the collagen fibrils have a bulk density in the range of from about 1.5 to about 3.5 lbs/ft$^3$.

18. The product of claim 14, wherein the collagen slurry has a collagen concentration in the range of about 5% to about 8% (weight/volume).

19. The product of claim 14, wherein the process comprises the further step of
   (c) introducing the collagen fiber into a second dehydrating bath.

20. The product of claim 19, wherein the first dehydrating bath is an ammonia bath and the second dehydrating bath is an ammonia/acetone bath.

21. The product of claim 14, wherein the process further comprises the step of drying the collagen fiber.

22. A collagen fiber prepared by the process comprising:
   (a) suspending a plurality of collagen fibrils in water to form a collagen slurry;
   (b) homogenizing the collagen slurry;
   (c) filtering the homogenized collagen slurry; and
   (d) extruding the filtered collagen slurry into a first dehydrating bath to at least partially dehydrate the collagen slurry and thereby form a collagen fiber.

23. The product of claim 22, wherein the collagen fibrils comprise microfibrillar collagen fibrils.

24. The product of claim 22, wherein the collagen fibrils comprise a collagen flour.

25. The product of claim 22, wherein the collagen fibrils have a bulk density in the range of from about 1.5 to about 3.5 lbs/ft$^3$.

26. The product of claim 22, wherein the collagen slurry has a collagen concentration in the range of about 5% to about 8% (weight/volume).

27. The collagen fiber of claim 22, wherein the fiber is prepared by the process comprising:
   extruding a collagen slurry containing collagen fibrils into a dehydrating bath.

28. A hemostatic fabric comprising the collagen fibers according to claim 22.

29. A sterile package containing a hemostatic fabric according to claim 28.

30. A method for promoting hemostasis comprising, manually pressing a hemostatic fabric of claim 28 against a bleeding surface for a period of time until clotting has occurred at the interface between the hemostatic fabric and the surface.

31. The method of claim 30, wherein the bleeding surface is selected from the group consisting of a parenchymal organ, a spine and a brain.

32. The method of claim 1, wherein the collagen concentration is about 2%.

33. The method of claim 14, wherein the collagen concentration is about 2%.

34. A method for forming a collagen fiber comprising:
(a) suspending a plurality of collagen fibrils in water to form a collagen slurry;
(b) homogenizing the collagen slurry;
(c) filtering the homogenized collagen slurry; and
(d) extruding the filtered collagen slurry into a first dehydrating bath to at least partially dehydrate the collagen slurry and thereby form a collagen fiber.

35. The method of claim 34, wherein the collagen concentration of the collagen slurry in step (a) is about 2%.

36. The method of claim 34, wherein the first dehydrating bath comprises an ammonia/acetone bath.

37. The method of claim 34, further comprising the step of introducing the collagen fiber into a second dehydrating bath.

38. The method of claim 37, wherein the second dehydrating bath is an acetone bath.

39. The method of claim 34, further comprising the step of drying the collagen fiber.

40. The method of claim 34, further comprising the step of forming the collagen fiber into a hemostatic fabric.

41. The method of claim 34, further comprising the step of degassing the collagen slurry prior to forming the collagen fiber.

42. The method of claim 34, comprising the further step of introducing a hemostatic agent into the fiber.

43. The method of claim 34, comprising the further step of introducing a therapeutic agent into the fiber.

44. A collagen fiber prepared by the process comprising:
(a) suspending a plurality of collagen fibrils in water to form a collagen slurry;
(b) filtering the collagen slurry; and
(c) extruding the filtered collagen slurry into a first dehydrating bath to at least partially dehydrate the collagen slurry and thereby form a collagen fiber.

45. The product of claim 44, wherein the collagen fibrils comprise microfibrillar collagen fibrils.

46. The product of claim 44, wherein the collagen fibrils comprise a collagen flour.

47. The product of claim 44, wherein the collagen fibrils have a bulk density in the range of from about 1.5 to about 3.5 lbs/ft$^3$.

48. The product of claim 44, wherein the collagen slurry has a collagen concentration in the range of about 5% to about 8% (weight/volume).

49. The collagen fiber of claim 44, wherein the fiber is prepared by the process comprising:
extruding a collagen slurry containing collagen fibrils into a dehydrating bath.

50. A hemostatic fabric comprising the collagen fibers according to claim 44.

51. A sterile package containing a hemostatic fabric according to claim 50.

52. A method for promoting hemostasis comprising, manually pressing a hemostatic fabric of claim 50 against a bleeding surface for a period of time until clotting has occurred at the interface between the hemostatic fabric and the surface.

53. The method of claim 52, wherein the bleeding surface is selected from the group consisting of a parenchymal organ, a spine and a brain.

54. A method for forming a collagen fiber comprising:
(a) suspending a plurality of collagen fibrils in water to form a collagen slurry;
(b) filtering the collagen slurry; and
(c) extruding the filtered collagen slurry into a first dehydrating bath to at least partially dehydrate the collagen slurry and thereby form a collagen fiber.

55. The method of claim 54, wherein the collagen concentration of the collagen slurry in step (a) is about 2%.

56. The method of claim 54, wherein the first dehydrating bath comprises an ammonia/acetone bath.

57. The method of claim 54, further comprising the step of introducing the collagen fiber into a second dehydrating bath.

58. The method of claim 57 wherein the second dehydrating bath is an acetone bath.

59. The method of claim 54, further comprising the step of drying the collagen fiber.

60. The method of claim 54, further comprising the step of forming the collagen fiber into a hemostatic fabric.

61. The method of claim 54, further comprising the step of degassing the collagen slurry prior to forming the collagen fiber.

62. The method of claim 54, comprising the further step of introducing a hemostatic agent into the fiber.

63. The method of claim 54, comprising the further step of introducing a therapeutic agent into the fiber.

64. A collagen fiber prepared by the process comprising:
(a) suspending a plurality of collagen fibrils in water to form a collagen slurry;
(b) homogenizing the collagen slurry; and
(c) extruding the homogenized collagen slurry into a first dehydrating bath to at least partially dehydrate the collagen slurry and thereby form a collagen fiber.

65. The product of claim 64, wherein the collagen fibrils comprise microfibrillar collagen fibrils.

66. The product of claim 64, wherein the collagen fibrils comprise a collagen flour.

67. The product of claim 64, wherein the collagen fibrils have a bulk density in the range of from about 1.5 to about 3.5 lbs/ft$^3$.

68. The product of claim 64, wherein the collagen slurry has a collagen concentration in the range of about 5% to about 8% (weight/volume).

69. The collagen fiber of claim 64, wherein the fiber is prepared by the process comprising:
extruding a collagen slurry containing collagen fibrils into a dehydrating bath.

70. A hemostatic fabric comprising the collagen fibers according to claim 64.

71. A sterile package containing a hemostatic fabric according to claim 70.

72. A method for promoting hemostasis comprising, manually pressing a hemostatic fabric of claim 70 against a bleeding surface for a period of time until clotting has occurred at the interface between the hemostatic fabric and the surface.

73. The method of claim 72, wherein the bleeding surface is selected from the group consisting of a parenchymal organ, a spine and a brain.

74. A method for forming a collagen fiber comprising:
(a) suspending a plurality of collagen fibrils in water to form a collagen slurry;
(b) homogenizing the collagen slurry;

(c) extruding the homogenized collagen slurry into a first dehydrating bath to at least partially dehydrate the collagen slurry and thereby form a collagen fiber.

75. The method of claim 74, wherein the collagen concentration of the collagen slurry in step (a) is about 2%.

76. The method of claim 74, wherein the first dehydrating bath comprises an ammonia/acetone bath.

77. The method of claim 74, further comprising the step of introducing the collagen fiber into a second dehydrating bath.

78. The method of claim 77, wherein the second dehydrating bath is an acetone bath.

79. The method of claim 74, further comprising the step of drying the collagen fiber.

80. The method of claim 74, further comprising the step of forming the collagen fiber into a hemostatic fabric.

81. The method of claim 74, further comprising the step of degassing the collagen slurry prior to forming the collagen fiber.

82. The method of claim 74, comprising the further step of introducing a hemostatic agent into the fiber.

83. The method of claim 74, comprising the further step of introducing a therapeutic agent into the fiber.

* * * * *